United States Patent
Dave et al.

(10) Patent No.: US 9,445,591 B2
(45) Date of Patent: *Sep. 20, 2016

(54) SOLID HERBICIDE COMPOSITIONS WITH BUILT-IN ADJUVANT

(71) Applicant: DOW AGROSCIENCES LLC, Indianapolis, IN (US)

(72) Inventors: Hiteshkumar Dave, Carmel, IN (US); Lei Liu, Carmel, IN (US); Mei Li, Westfield, IN (US); David Ouse, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/749,415

(22) Filed: Jan. 24, 2013

(65) Prior Publication Data

US 2013/0190176 A1 Jul. 25, 2013

Related U.S. Application Data

(60) Provisional application No. 61/590,388, filed on Jan. 25, 2012.

(51) Int. Cl.

| | | |
|---|---|---|
| *A61K 9/14* | (2006.01) | |
| *A61K 9/50* | (2006.01) | |
| *A01N 43/40* | (2006.01) | |
| *A01N 43/60* | (2006.01) | |
| *A01N 43/54* | (2006.01) | |
| *A01N 43/90* | (2006.01) | |
| *A01N 43/76* | (2006.01) | |
| *A01N 37/00* | (2006.01) | |
| *A01N 37/34* | (2006.01) | |
| *A01N 25/14* | (2006.01) | |
| *A01N 39/02* | (2006.01) | |

(52) U.S. Cl.
CPC ............... *A01N 43/54* (2013.01); *A01N 25/14* (2013.01); *A01N 39/02* (2013.01); *A01N 43/40* (2013.01)

(58) Field of Classification Search
None
See application file for complete search history.

(56) References Cited

U.S. PATENT DOCUMENTS

| | | | |
|---|---|---|---|
| 5,137,726 A | 8/1992 | Ogawa et al. | |
| 5,703,010 A * | 12/1997 | Heinrich et al. | 504/361 |
| 8,449,917 B2 * | 5/2013 | Dave et al. | 424/489 |
| 2009/0197765 A1 * | 8/2009 | Gaytan et al. | 504/130 |
| 2010/0144526 A1 * | 6/2010 | Ohno et al. | 504/134 |
| 2010/0167930 A1 * | 7/2010 | Koivunen et al. | 504/136 |
| 2011/0098181 A1 | 4/2011 | Mann et al. | |
| 2012/0015811 A1 | 1/2012 | Dave et al. | |
| 2013/0023414 A1 * | 1/2013 | Dave et al. | 504/103 |
| 2013/0109569 A1 * | 5/2013 | Dave et al. | 504/130 |

FOREIGN PATENT DOCUMENTS

| | | |
|---|---|---|
| CN | 101530106 A | 9/2009 |
| JP | 9194302 A | 7/1997 |
| JP | 9194302 B2 | 7/1997 |
| WO | WO 02/074080 | 9/2002 |
| WO | WO 2007/027863 | 3/2007 |
| WO | WO 2009/012979 A2 | 1/2009 |
| WO | WO 2009/058717 A2 | 5/2009 |
| WO | WO 2012/177851 | 12/2012 |

OTHER PUBLICATIONS

Kaloumenos et al., Weed Science Society of America, vol. 23 issue 3, 2009, pp. 470-476 teaches that nicosulfuron is an ACCase inhibiting herbicide).—ABS.*

* cited by examiner

*Primary Examiner* — Alton Pryor
(74) *Attorney, Agent, or Firm* — Michael R. Asam; Meunier Carlin & Curfman, LLC

(57) ABSTRACT

The present disclosure concerns improved solid herbicidal compositions, such as granules and powders, containing built-in adjuvant, which have improved stability and exhibit acceptable herbicidal efficacy when used to control weeds in flooded rice paddies or fields, or cereal crop fields.

27 Claims, 1 Drawing Sheet

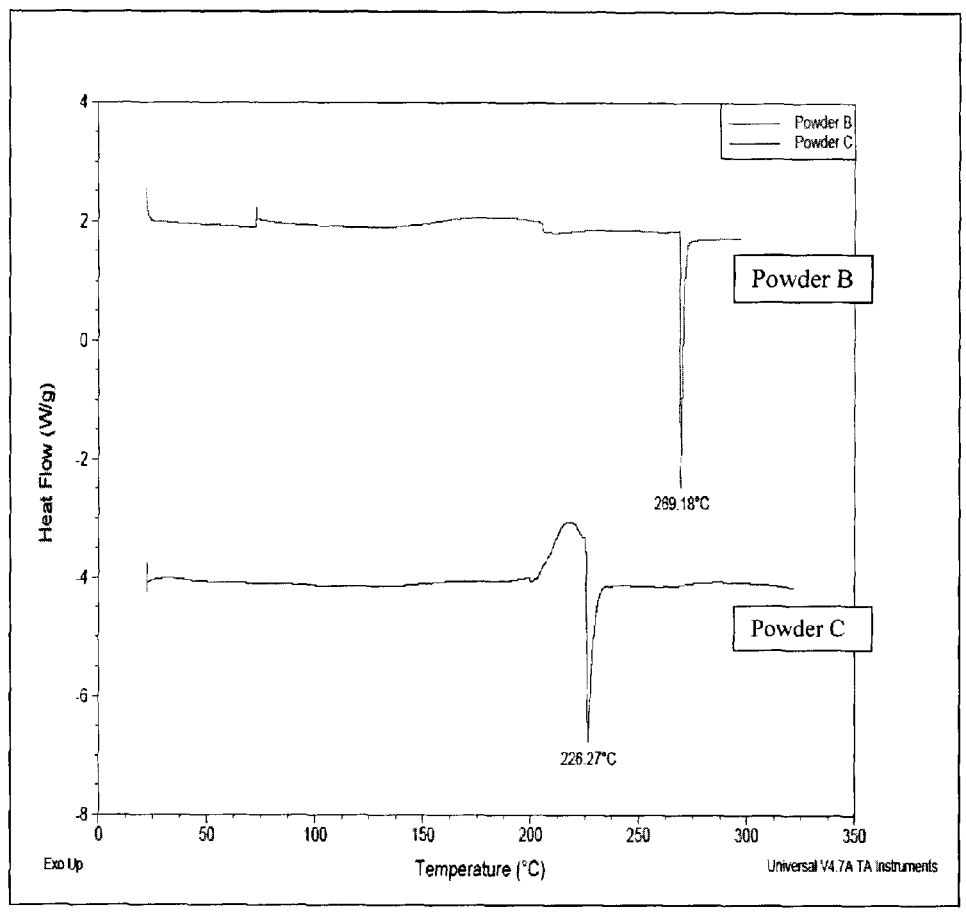

SOLID HERBICIDE COMPOSITIONS WITH BUILT-IN ADJUVANT

CROSS-REFERENCE TO RELATED APPLICATION

This application claims priority to U.S. Provisional Patent Application Ser. No. 61/590,388, filed Jan. 25, 2012, the disclosure of which is incorporated herein by reference in its entirety.

FIELD

Provided herein are improved solid herbicidal compositions, such as granules and powders, comprising one or more herbicide and one or more built-in adjuvant, and methods for their preparation and use. Such improved solid compositions exhibit improved stability and acceptable herbicidal efficacy on weeds in various crops.

BACKGROUND

Agrochemical formulations are generally designed based on customer needs and the physiochemical properties of the active ingredients, for example, the solubility of the active ingredient in water or non-aqueous solvents. There are two major categories of formulations, solid formulations and liquid formulations.

Granule products containing agricultural active ingredients represent one class of solid formulations that are seeing increased use today because of their relative safety compared to liquid formulations and because of the advantages they offer with regard to cost savings in packaging and transportation. Granule products, e.g., in the form of emulsifiable granules (EG), water dispersible granules (DG), and granules (GR) for broadcast application may be used for insect, weed, fungal pathogen and nematode control and are often used in soil and aquatic environments. Because of the particle weight, granules used in aerial applications may pose a reduced hazard from off-target drift compared to aerial liquid spray applications.

Powder or wettable powder (WP) products containing agricultural active ingredients represent additional classes of solid formulations that are also used in agriculture and differ from granules primarily by their smaller particle size. Granules typically have a size range between about 200 to about 4000 micrometers (Wikipedia: Granulation—making of granules) and are much larger than the particles in powder formulations and therefore present less of a respiratory hazard. Granule products may be produced from powders or wettable powders in a granulation or agglomeration process.

Active ingredients, in the form of solids or liquids, may be formulated as granules, and include insecticides, herbicides, fungicides, nematicides and plant growth regulators. Granule formulations usually contain a relatively small amount of the active ingredients since the granules are frequently not further diluted with a carrier solvent such as water prior to use, but are instead applied directly to the area of interest, such as, for example, soil or water. Once applied, the active ingredients contained in the granules are released to the area of application, typically upon exposure to water.

Agricultural granules containing active ingredients also contain solid inert ingredients that may serve as a diluent and/or help maintain the granules in a stable, solid state. These solid inert ingredients may include, for example, clays, starches, silicas, sulphates, chlorides, lignosulfonates, carbohydrates such as dextrines, alkylated celluloses, xanthum gums and guaseed gums, and synthetic polymers such as polyvinyl alcohols, sodium polyacrylates, polyethylene oxides, polyvinylpyrrolidones and urea/formaldehyde polymers like PergoPak® M (registered trademark of Albemarle Corporation). The active ingredient(s) contained in a granule may be melted into a liquid, dissolved in a solvent or dispersed in a liquid, which may then be sprayed onto or absorbed into the solid inert ingredients. In the absence of effective solid inert ingredients, dry granules may be physically unstable and, in the case of solid particles, slowly breakdown forming a dust or powder or, in the case of granules containing liquid built-in adjuvants, slowly breakdown forming large liquid droplets as a result of Ostwald Ripening. Many solid inert ingredients used in agricultural granule formulations generally have good water solubility or dispersibility.

Rice is an important cereal crop grown in many parts of the world and is cultivated under both wet and dry conditions. Control of weeds in rice is very important in order to maintain high levels of agricultural productivity. Use of herbicide granules for weed control in flooded rice paddies and fields is a very common agronomic practice in many rice growing regions. New herbicide granule products that offer improved performance relative to current products are needed.

Cyhalofop-butyl, (2R)-2-[4-(4-cyano-2-fluorophenoxy)phenoxy]propanoic acid butyl ester (CAS#122008-78-0), is a member of the aryloxyphenoxypropionic acid class of herbicides, which are known in the art as the fop herbicides, and is used to control grass weeds in rice. Cyhalofop-butyl is marketed as Clincher® herbicide (registered trademark of Dow AgroSciences LLC), and is sold in granule (GR), oil in water (EW) and emulsifiable concentrate (EC) formulations, and exhibits good selectivity to rice when used in both dry land and flooded paddy applications.

Existing commercial granule formulations of cyhalofop-butyl contain relatively large amounts of solid inert ingredients such as potassium chloride, clay or starch combined with relatively small amounts of built-in adjuvants such as aromatic solvents. The limited built-in adjuvant content of current granule products can limit the biological performance of cyhalofop-butyl herbicide due to a minimal herbicidal adjuvant effect.

Described herein is an improvement to the herbicidal granule or powder compositions disclosed in U.S. Patent Application Publication 2012/0015811A1, published Jan. 19, 2012. Such improved compositions show improved storage stability in various environments and offer acceptable herbicidal efficacy when used to control weeds in flooded rice paddies or fields, or other crops.

SUMMARY

In one embodiment, provided herein are improved solid herbicidal compositions containing built-in adjuvant with improved stability in humid and high compression environments, which comprises:

a) at least one herbicide, which is selected from the class of ACCase and ALS enzyme inhibitors, or selected from compounds of the Formula

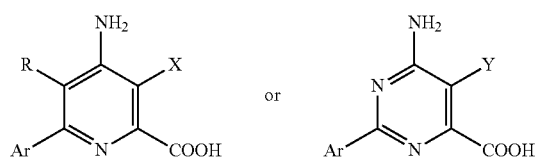

wherein
  Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;
  R represents H or F;
  X represents Cl or vinyl; and
  Y represents Cl, vinyl or methoxy;
  and their salts and esters;
  wherein the herbicide(s) is present in the composition in an amount of from about 1 gram per kilogram (g/kg) to about 200 g/kg relative to the total weight of the composition;
b) one or more built-in adjuvant, wherein the build-in adjuvant(s) is present in the composition in an amount of from about 50 g/kg to about 750 g/kg relative to the total weight of the composition; and
c) one or more solid, water soluble polymer or oligomer, wherein the solid, water soluble polymer(s) or oligomer(s) is present in the composition in an amount of from about 200 g/kg to about 700 g/kg relative to the total weight of the composition; and
  wherein the composition does not comprise solid carbohydrate.

The present disclosure equally well concerns improved herbicidal granules or improved herbicidal powders containing built-in adjuvant.

Also provided herein are methods of preparing the improved solid herbicidal compositions described herein.

Also provided herein are methods of using the improved solid herbicidal compositions described herein.

BRIEF DESCRIPTION OF THE FIGURES

FIG. 1 shows comparative Differential Scanning calorimetry (DSC) data (graphs of heat flow into or out of a sample vs. temperature) of one embodiment of the improved solid herbicidal composition described herein, Powder B (contains no carbohydrate), as compared with one embodiment of a reference composition, Powder C (contains carbohydrate).

DETAILED DESCRIPTION

Agricultural active ingredients that have low water solubility can sometimes be difficult to effectively apply to crops to eliminate pests. This situation is particularly challenging when the active ingredients are not applied directly to plant foliage, such as, for example, when herbicide granule products are used to control weeds in flooded paddy rice and other aquatic environments. Herbicide granules applied to flooded paddy rice are normally added directly to the water in the rice paddy and have very little direct contact with plant foliage during application. For example, cyhalofop-butyl is an herbicidal active ingredient that when applied to water in a granule, requires the use of a built-in adjuvant to provide the necessary delivery and uptake of the herbicide into the target weeds and expression of acceptable levels of weed control. Granules that are capable of containing high levels of built-in adjuvants can offer improved weed control in aquatic environments, such as, for example, flooded paddy rice, on a grams active ingredient per hectare (gai/ha) basis.

Solid agricultural products such as herbicide granules and powders can be susceptible to undesirable physical changes during preparation and storage, such as, for example, caking or sticking together of the granules or powders. Such physical changes can make granule and powder products difficult to handle, or difficult to disperse in water or blend with other granule or powder products. Proper screening of candidate solid agricultural compositions must be conducted under a variety of storage conditions in order to develop products with acceptable physical properties for use in today's agricultural chemical markets.

I. Improved Solid Compositions

In one embodiment, the improved solid herbicidal compositions provided herein comprise at least one herbicide active ingredient, one or more built-in adjuvant, and one or more solid, water soluble polymer or oligomer. In one embodiment, such improved solid herbicidal compositions provided herein do not comprise solid carbohydrate.

In one embodiment, provided herein is a solid herbicidal composition comprising:
a) at least one herbicide selected from the class of ACCase and ALS enzyme inhibitors and compounds of the Formula wherein
  Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;
  R represents H or F;
  X represents Cl or vinyl; and
  Y represents Cl, vinyl or methoxy;
  and their salts and esters;
  wherein the herbicide(s) is present in the composition in an amount of from about 1 gram per kilogram (g/kg) to about 200 g/kg relative to the total weight of the composition;
b) one or more built-in adjuvant, wherein the built-in adjuvant(s) is present in the composition in an amount of from about 50 g/kg to about 750 g/kg relative to the total weight of the composition; and
c) one or more solid, water soluble polymer or oligomer, wherein the solid, water soluble polymer(s) or oligomer(s) is present in the composition in an amount of from about 200 g/kg to about 700 g/kg relative to the total weight of the composition;
  wherein the composition does not comprise solid carbohydrate.

In one embodiment, the improved solid herbicidal compositions provided herein consist essentially of one or more herbicide active ingredient, one or more built-in adjuvant, and one or more solid, water soluble polymer or oligomer. In one embodiment, such improved solid herbicidal compositions provided herein may contain one or more additional agriculturally active ingredients, including but not limited to, pesticides, fungicides, insecticides, nematicides, plant growth regulators, and safeners; and/or one or more additional agriculturally acceptable excipient other than solid carbohydrate.

In one embodiment, provided herein is a solid herbicidal composition consisting essentially of:
a) at least one herbicide selected from the class of ACCase and ALS enzyme inhibitors and compounds of the Formula

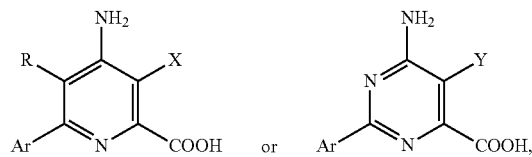

wherein
Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;
R represents H or F;
X represents Cl or vinyl; and
Y represents Cl, vinyl or methoxy;
and their salts and esters;
wherein the herbicide(s) is present in the composition in an amount of from about 1 gram per kilogram (g/kg) to about 200 g/kg relative to the total weight of the composition;
b) one or more built-in adjuvant, wherein the built-in adjuvant(s) is present in the composition in an amount of from about 50 g/kg to about 750 g/kg relative to the total weight of the composition; and
c) one or more solid, water soluble polymer or oligomer, wherein the solid, water soluble polymer(s) or oligomer(s) is present in the composition in an amount of from about 200 g/kg to about 700 g/kg relative to the total weight of the composition;
wherein the composition does not comprise solid carbohydrate.

In one embodiment, the improved solid herbicidal compositions provided herein consist of one or more herbicide active ingredient, one or more built-in adjuvant, and one or more solid, water soluble polymer or oligomer. In one embodiment, such improved solid herbicidal compositions provided herein do not contain solid carbohydrate, and may contain one or more additional agriculturally active ingredients, including but not limited to, pesticides, fungicides, insecticides, nematicides, plant growth regulators, and safeners, and/or one or more additional agriculturally acceptable excipient.

In one embodiment, provided herein is a solid herbicidal composition consisting of:
a) at least one herbicide selected from the class of ACCase and ALS enzyme inhibitors and compounds of the Formula

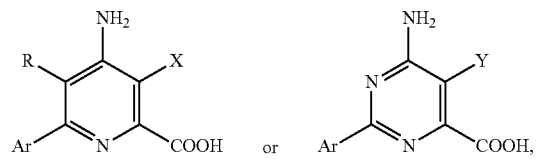

wherein
Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;
R represents H or F;
X represents Cl or vinyl; and
Y represents Cl, vinyl or methoxy;
and their salts and esters;
wherein the herbicide(s) is present in the composition in an amount of from about 1 gram per kilogram (g/kg) to about 200 g/kg relative to the total weight of the composition;
b) one or more built-in adjuvant, wherein the built-in adjuvant(s) is present in the composition in an amount of from about 50 g/kg to about 750 g/kg relative to the total weight of the composition; and
c) one or more solid, water soluble polymer or oligomer, wherein the solid, water soluble polymer(s) or oligomer(s) is present in the composition in an amount of from about 200 g/kg to about 700 g/kg relative to the total weight of the composition;
wherein the composition does not comprise solid carbohydrate.

In one embodiment, without being limited by theory, the presence of at least about 200 g/kg of one or more solid, water soluble polymers or oligomers in the compositions provided herein provides stabilized compositions containing high levels of built-in adjuvants. The improved solid herbicidal compositions provided herein omit the solid carbohydrate ingredient in reference compositions, which can, under certain conditions, cause instability.

The improved solid herbicidal compositions described herein include those solid agricultural compositions containing active ingredients and inert ingredients, and include granules, dispersible granules, emulsifiable granules, powders, wettable powders, and the like. In one embodiment, the improved solid herbicidal composition described herein is a granule. In one embodiment, the improved solid herbicidal composition described herein is a powder. In one embodiment, the improved solid herbicidal compositions described herein further comprise one or more additional inert ingredients. In one embodiment, the improved solid herbicidal compositions described herein further comprise one or more additional agriculturally active ingredients (e.g., pesticides, herbicides, fungicides, insecticides, nematicides, plant growth regulators, or safeners).

The improved solid herbicidal compositions described herein have been surprisingly found to show improved stability upon removal of the solid carbohydrate ingredient present in reference compositions. Stable solid herbicidal compositions are generally defined as those that are stable physically and chemically to the environments in which they are produced and stored. By removing the solid carbohydrate ingredient present in reference compositions, the improved compositions described herein can better retain their original physical form and are less susceptible to undesirable physical changes that might prevent them from being free-flowing and easy to handle and apply to crops.

In certain embodiments, provided herein are improved solid herbicidal compositions containing built-in adjuvant with improved stability in humid and high compression environments, which comprises:

a) at least one herbicide, which is selected from the class of ACCase and ALS enzyme inhibitors, or selected from compounds of the Formula

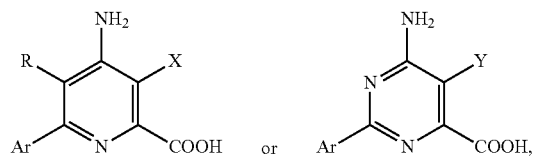

wherein
Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;
R represents H or F;
X represents Cl or vinyl; and
Y represents Cl, vinyl or methoxy;
and their salts and esters;
wherein the herbicide(s) is present in the composition in an amount of from about 1 g/kg to about 200 g/kg relative to the total weight of the composition;

b) one or more built-in adjuvant, wherein the build-in adjuvant(s) is present in the composition in an amount of from about 50 g/kg to about 750 g/kg relative to the total weight of the composition;

c) one or more solid carbohydrate, wherein the solid carbohydrate(s) is present in the composition in an amount of from about 10 g/kg to about 700 g/kg relative to the total weight of the composition; and d) one or more solid, water soluble polymer or oligomer, wherein the solid, water soluble polymer(s) or oligomer(s) is present in the composition in an amount of from about 50 g/kg to about 700 g/kg relative to the total weight of the composition, with the proviso that the total amount of the solid carbohydrate and the solid, water soluble polymer or oligomer is at least about 200 g/kg relative to the total weight of the composition;

wherein the improvement comprises removing the solid carbohydrate (c) with the proviso that the solid, water soluble polymer or oligomer (d) is present in an amount of at least about 200 g/kg relative to the total weight of the composition.

As used herein, unless otherwise indicated, solid carbohydrates are defined as monosaccharides, disaccharides or polysaccharides, or mixtures thereof, with good water solubility or dispersibility. However, as used herein, solid carbohydrates do not include any non-sugar compound (e.g., a polymer or oligomer, or an adjuvant), even if such non-sugar compound is covalently linked to or non-covalently complexed with carbohydrate(s). Moreover, it should be understood that certain solid herbicidal compositions having a trace amount of solid carbohydrates (e.g., less than 10 g/kg, less than 9 g/kg, less than 8 g/kg, less than 7 g/kg, less than 6 g/kg, less than 5 g/kg, less than 4 g/kg, less than 3 g/kg, less than 2 g/kg, or less than 1 g/kg,) are considered as equivalent to the improved solid herbicidal compositions provided herein. Therefore, the phrases, such as "do not comprise solid carbohydrate," "do not contain solid carbohydrate," "omit solid carbohydrate," or "removal of solid carbohydrate," as used herein, mean that there is no significant amount of solid carbohydrate present (e.g., no greater than 10 g/kg, no greater than 9 g/kg, no greater than 8 g/kg, no greater than 7 g/kg, no greater than 6 g/kg, no greater than 5 g/kg, no greater than 4 g/kg, no greater than 3 g/kg, no greater than 2 g/kg, or no greater than 1 g/kg relative to the total weight of the composition).

A. Herbicide Active Ingredients

In one embodiment, the herbicide active ingredients of the improved solid herbicidal compositions provided herein may be selected from the ACCase (acetyl coenzyme A carboxylase) enzyme inhibitor class of herbicides and the ALS (acetolactate synthase) enzyme inhibitor class of herbicides. The ACCase inhibiting herbicide active ingredients which are known in the art as the "fop" and "dim" herbicides include, but are not limited to, clethodim, clodinafop-propargyl, cycloxydim, cyhalofop-butyl, fenoxaprop-ethyl, fluazifop-P-butyl, haloxyfop-methyl, haloxyfop-P-methyl, metamifop, propaquizafop, quizalofop-P-ethyl, quizalofop-P-tefuryl, profoxydim, sethoxydim and tralkoxydim and derivatives thereof. The ALS inhibiting herbicide active ingredients include, but are not limited to, azimsulfuron, bensulfuron-methyl, bispyribac-Na, cinosulfuron, cloransulam-methyl, cyclosulfamuron, diclosulam, ethoxysulfuron, florasulam, flucetosulfuron, flumetsulam, halosulfuron-methyl, metazosulfuron, metosulam, metsulfuron-methyl, penoxsulam, primisulfuron-methyl, propyrisulfuron, pyrazosulfuron-ethyl, pyribenzoxim, pyriftalid, pyriminobac-methyl, pyrimisulfan, pyroxsulam, imazamox, imazapyr, imazethapyr, imazosulfuron and triafamone and derivatives thereof.

In one embodiment, the herbicide active ingredients of the improved solid herbicidal compositions provided herein have a water solubility of less than about 3000 ppm, less than about 1000 ppm, or less than about 100 ppm. In one embodiment, the herbicide active ingredients of the improved solid herbicidal compositions provided herein have a water solubility of less than about 20000 parts per million (ppm), less than about 10000 ppm, less than about 5000 ppm, less than about 4000 ppm, less than about 2000 ppm, less than about 500 ppm, or less than about 200 ppm.

In one embodiment, the herbicide active ingredient(s) is(are) present in the composition in an amount of from about 1 g/kg to about 200 g/kg or from about 2 g/kg to about 75 g/kg relative to the total weight of the composition. In one embodiment, the herbicide active ingredient(s) is(are) present in the composition in an amount of from about 1 g/kg to about 150 g/kg, from about 1 g/kg to about 125 g/kg, from about 1 g/kg to about 100 g/kg, from about 1 g/kg to about 75 g/kg, from about 3 g/kg to about 75 g/kg, from about 5 g/kg to about 75 g/kg, from about 10 g/kg to about 75 g/kg, from about 15 g/kg to about 75 g/kg relative to the total weight of the composition.

In some embodiments, the improved solid herbicidal compositions provided herein contain at least one of cyhalofop-butyl, penoxsulam, bensulfuron-methyl, azimsulfuron, imazosulfuron, and fenoxaprop-P-ethyl. In some embodiments, the improved solid herbicidal compositions provided herein contain at least one of cyhalofop-butyl, penoxsulam, and bensulfuron-methyl.

In some embodiments, the herbicide active ingredients of the improved solid herbicidal compositions provided herein may be selected from compounds of the Formula

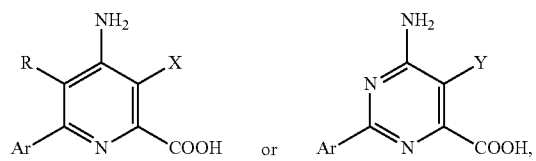

wherein
  Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;
  R represents H or F;
  X represents Cl or vinyl; and
  Y represents Cl, vinyl or methoxy;
and their salts and esters, as disclosed, for example, in U.S. Pat. Nos. 7314849 B2, 7300907 B2, 7786044 B2 and 7642220 B2, all of which are incorporated herein by reference.

In specific embodiment, suitable herbicides include a compound of the Formula

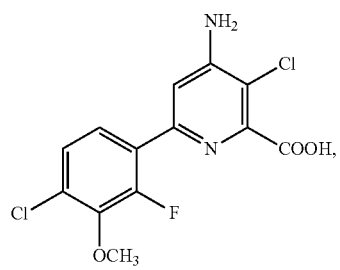 [SMILES: COc1c(Cl)ccc(-c2cc(N)c(Cl)c(C(=O)O)n2)c1F]

and its $C_1$-$C_6$ alkyl esters or salt derivatives, such as, for example, the methyl ester, referred to herein as Compound A.

In specific embodiment, suitable herbicides include a compound of the Formula

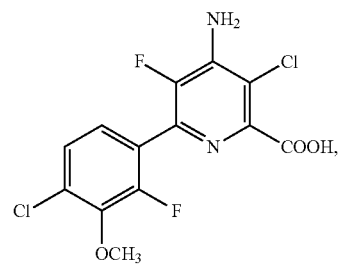 [SMILES: COc1c(Cl)ccc(-c2nc(C(=O)O)c(Cl)c(N)c2F)c1F]

and its $C_1$-$C_{12}$ alkyl and $C_7$-$C_{12}$ arylalkyl esters or salt derivatives, such as, for example, the benzyl ester, referred to herein as Compound B.

In some embodiments, the improved solid herbicidal compositions described herein comprise, as herbicide active ingredients, the compound of the Formula

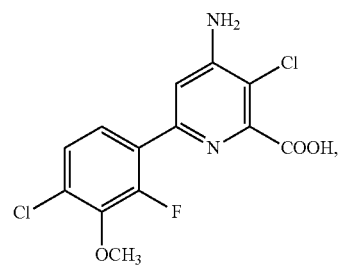 [SMILES: COc1c(Cl)ccc(-c2cc(N)c(Cl)c(C(=O)O)n2)c1F]

or a $C_1$-$C_6$ alkyl ester or salt derivative thereof, such as, for example, the methyl ester, and at least one of cyhalofop-butyl, diclosulam, chloransulam-methyl, florasulam, penoxsulam, pyroxsulam, bensulfuron-methyl, azimsulfuron, imazosulfuron, or fenoxaprop-P-ethyl.

In some embodiments, the improved solid herbicidal compositions described herein comprise, as herbicide active ingredients, the compound of the Formula

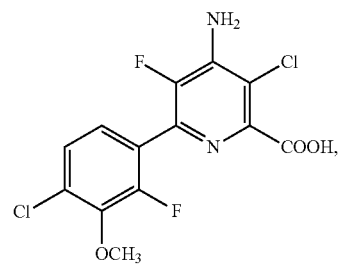 [SMILES: COc1c(Cl)ccc(-c2nc(C(=O)O)c(Cl)c(N)c2F)c1F]

or a $C_1$-$C_{12}$ alkyl or $C_7$-$C_{12}$ arylalkyl ester or salt derivative thereof, such as, for example, the benzyl ester, and at least one of cyhalofop-butyl, fenoxaprop-ethyl, haloxyfop-P-methyl, metamifop, profoxydim, azimsulfuron, bensulfuron-methyl, bispyribac-Na, ethoxysulfuron, flucetosulfuron, halosulfuron-methyl, iofensulfuron, metazosulfuron, metsulfuron-methyl, penoxsulam, propyrisulfuron, pyrazosulfuron-ethyl, pyribenzoxim, pyriftalid, pyrimisulfan, imazosulfuron, or triafamone.

B. Built-in Adjuvant

Adjuvants are important ingredients in agricultural chemical products and may be defined as substances which can increase the biological activity of the active ingredient, but are themselves not significantly biologically active. Adjuvants assist with the effectiveness of the active ingredient, such as, for example, by improving the delivery and uptake of an herbicide into a target weed plant leading to improved biological control.

Adjuvants, in the form of solids or liquids, can be added directly to a formulated agricultural product, such as a granule, to provide improved performance of the product upon application. Commonly used adjuvants may include, for example, surfactants, spreaders, petroleum and plant derived oils and solvents and wetting agents. Examples of commonly used adjuvants include, but are not limited to, paraffin oil, horticultural spray oils (e.g., summer oil), methylated rape seed oil, methylated soybean oil, highly refined vegetable oil and the like, polyol fatty acid esters, polyethoxylated esters, ethoxylated alcohols, alkyl polysaccharides and blends, amine ethoxylates, sorbitan fatty acid ester ethoxylates, polyethylene glycol esters, organosilicone based surfactants, ethylene vinyl acetate terpolymers, ethoxylated alkyl aryl phosphate esters and the like. These and other adjuvants are described in the "*Compendium of Herbicide Adjuvants, 9th Edition,*" edited by Bryan Young, Dept. of Plant, Soil and Agricultural Systems, Southern Illinois University MC-4415, 1205 Lincoln Drive, Carbondale, Ill. 62901, which is available for viewing on the interne at http://www.herbicide-adjuvants.com/.

The term "built-in adjuvant" refers to one or more adjuvants that have been added to a particular formulation, such as a granule or liquid formulation, at the manufacturing stage of the product, rather than at the point of use of the product such as, for example, to a spray solution. The use of built-in adjuvants simplifies the use of agrochemical products for the end-user by reducing the number of ingredients that must be individually measured and applied.

The built-in adjuvants of the described improved solid herbicidal compositions can be in the form of a liquid or a solid, and may include one or more of a non-ionic surfactant or a water immiscible liquid. In one embodiment, the built-in adjuvant of the described improved solid herbicidal compositions is one or more of water-immiscible liquid. In one embodiment, the built-in adjuvant of the described improved solid herbicidal compositions is one or more of non-ionic surfactant.

Non-ionic surfactants that may be used as built-in adjuvants include, but are not limited to, polyol fatty acid esters, polyethoxylated esters, polyethoxylated alcohols, alkyl polysaccharides such as alkyl polyglycosides and blends thereof, amine ethoxylates, sorbitan fatty acid ester ethoxylates, organosilicone based surfactants, ethylene vinyl acetate terpolymers, ethoxylated alkyl aryl phosphate esters and sucrose esters of fatty acids.

Water immiscible liquids that may be used as built-in adjuvants generally have less than about 1 volume percent solubility in water and may include, but are not limited to, petroleum fractions or hydrocarbons such as mineral oil, kerosene, paraffinic oils, mixed naphthalene and alkyl naphthalene fractions, aromatic solvents, particularly alkyl substituted benzenes such as xylene or propylbenzene fractions, and the like; plant derived oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above plant derived oils such as 2-ethyl hexyl stearate, n-butyl oleate, isopropyl myristate, propylene glycol dioleate and the like; and esters of diacids such as di-octyl succinate, di-butyl adipate, di-octyl phthalate, ditridecyl phthalate and the like.

In certain embodiments, built-in adjuvants include one or more of petroleum fractions or hydrocarbons such as mineral oil, paraffinic oils and aromatic solvents like xylene, propylbenzene fractions, alkyl naphthalene fractions, and the like; plant derived oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; $C_1$-$C_6$ esters of plant derived oils such as methylated seed oils; esters of diacids such as di-octyl succinate, di-butyl adipate, di-octyl phthalate, ditridecyl phthalate and the like; polyol fatty acid esters, polyethoxylated esters, polyethoxylated alcohols, alkyl polysaccharides such as alkyl polyglycosides and blends thereof, amine ethoxylates, sorbitan fatty acid ester ethoxylates, organosilicone based surfactants, ethylene vinyl acetate terpolymers, ethoxylated alkyl aryl phosphate esters and sucrose esters of fatty acids.

In some embodiments, the built-in adjuvant of the described improved solid herbicidal compositions is one or more of a petroleum derived paraffinic hydrocarbon, a petroleum derived aromatic hydrocarbon, a plant derived oil, or a $C_1$-$C_6$ ester of a plant derived oil. In some embodiments, the built-in adjuvant of the described improved solid herbicidal compositions is one or more of a seed oil, or a $C_1$-$C_6$ esters of plant derived oil. In some embodiments, the built-in adjuvant of the described improved solid herbicidal compositions is methyl soyate.

In some embodiments, the built-in adjuvants of the described improved solid herbicidal compositions are present in the composition in an amount of from about 50 g/kg to about 750 g/kg, from about 200 g/kg to about 600 g/kg, or from about 300 g/kg to about 600 g/kg relative to the total weight of the composition.

In some embodiments, the built-in adjuvants of the described improved solid herbicidal compositions are present in the composition in an amount of from about 100 g/kg to about 700 g/kg, from about 150 g/kg to about 650 g/kg, from about 200 g/kg to about 650 g/kg, from about 200 g/kg to about 600 g/kg, from about 250 g/kg to about 600 g/kg, from about 300 g/kg to about 600 g/kg, from about 325 g/kg to about 550 g/kg, from about 350 g/kg to about 500 g/kg, from about 375 g/kg to about 450 g/kg, from about 375 g/kg to about 425 g/kg, or from about 380 g/kg to about 420 g/kg relative to the total weight of the composition. In some embodiments, the amount of the build-in adjuvants in the composition is from about 75 g/kg to about 750 g/kg, from about 100 g/kg to about 750 g/kg, from about 125 g/kg to about 750 g/kg, from about 150 g/kg to about 750 g/kg, from about 200 g/kg to about 750 g/kg, from about 250 g/kg to about 750 g/kg, from about 300 g/kg to about 750 g/kg, from about 350 g/kg to about 750 g/kg, from about 300 g/kg to about 700 g/kg, from about 300 g/kg to about 600 g/kg, from about 300 g/kg to about 550 g/kg, or from about 300 g/kg to about 500 g/kg relative to the total weight of the composition.

In some embodiments, the improved solid herbicidal compositions provided herein do not contain methylnaphthalene. In some embodiments, when the improved solid herbicidal compositions provided herein comprise polyvinyl alcohol, the improved solid herbicidal compositions do not contain methylnaphthalene.

C. Solid, Water Soluble Polymer or Oligomer

The solid, water soluble polymers or oligomers of the described improved solid herbicidal compositions include one or more of a synthetic or partially synthetic polymer or oligomer that swells, disperses or dissolves in water at ambient temperature. Typical solid, water soluble polymers or oligomers include lignosulfonates, alkyl naphthalene sulfonate formaldehyde condensates, polyvinyl alcohols, polyacrylates, polyethylene oxides, and polyvinylpyrrolidones, and co-polymers, derivatives and mixtures thereof.

In certain embodiments, solid, water soluble polymers or oligomers of the described improved solid herbicidal compositions include polyvinyl alcohols derived from the hydrolysis of polyvinyl acetate, that vary in the degree of hydrolysis from about 87 to about 99%, of which Selvol® 205 (registered trademark of Sekisui Chemical Co., Ltd.) is an example, lignosulfonates, e.g., sodium lignosulfonate, of which Borresperse® NA (registered trademark of Borregaard LignoTech) is an example, and alkyl naphthalene sulfonate formaldehyde condensates, of which Morwet® D425 (registered trademark of Akzo Nobel) is an example, and co-polymers, derivatives and mixtures thereof.

In certain embodiments, the solid, water soluble polymer or oligomer of the described improved solid herbicidal compositions is one or more of a lignosulfonate, a polyvinyl alcohol with a degree of hydrolysis from about 87 to about 99 percent, or an alkyl naphthalene sulfonate formaldehyde condensate. In certain embodiments, the solid, water soluble polymer or oligomer of the described improved solid herbicidal compositions is one or more of a polyvinyl alcohol or a lignosulfonate. In certain embodiments, the solid, water soluble polymer or oligomer of the described improved solid herbicidal compositions is one or more of a polyvinyl alcohol derived from the hydrolysis of polyvinyl acetate, that vary in the degree of hydrolysis from about 87 to about 99%.

In one embodiment, the solid, water soluble polymers or oligomers of the described improved solid herbicidal compositions are present in the composition in an amount of from about 200 g/kg to about 700 g/kg, or from about 200 g/kg to about 600 g/kg relative to the total weight of the composition.

In one embodiment, the solid, water soluble polymers or oligomers of the described improved solid herbicidal compositions are present in the composition in an amount of from about 250 g/kg to about 650 g/kg, from about 300 g/kg to about 600 g/kg, from about 325 g/kg to about 550 g/kg, from about 350 g/kg to about 525 g/kg, from about 375 g/kg to about 500 g/kg, from about 400 g/kg to about 475 g/kg, or from about 425 g/kg to about 450 g/kg relative to the total weight of the composition. In one embodiment, the solid, water soluble polymers or oligomers of the described improved solid herbicidal compositions are present in the composition in an amount of from about 200 g/kg to about 650 g/kg, from about 200 g/kg to about 600 g/kg, from about 200 g/kg to about 550 g/kg, from about 200 g/kg to about 500 g/kg, from about 200 g/kg to about 450 g/kg, from about 200 g/kg to about 400 g/kg, from about 200 g/kg to about 300 g/kg, from about 250 g/kg to about 650 g/kg, from about 250 g/kg to about 600 g/kg, from about 250 g/kg to about 550 g/kg, from about 250 g/kg to about 500 g/kg, from about 250 g/kg to about 450 g/kg, from about 250 g/kg to about 400 g/kg, from about 300 g/kg to about 650 g/kg, from about 300 g/kg to about 600 g/kg, from about 300 g/kg to about 550 g/kg, or from about 300 g/kg to about 500 g/kg relative to the total weight of the composition.

In some embodiments, the improved solid herbicidal compositions provided herein contain no polyvinyl alcohol. In some embodiments, the improved solid herbicidal compositions provided herein contain polyvinyl alcohol, wherein the polyvinyl alcohol has a degree of hydrolysis of from about 87 to about 99 mol %. In some embodiments, the improved solid herbicidal compositions provided herein contain polyvinyl alcohol in an amount of less than about 20%, less than about 15%, less than about 10%, less than about 9%, less than about 8%, less than about 7%, less than about 6%, less than about 5%, less than about 4%, less than about 3%, less than about 2%, or less than about 1% w/w relative to the total weight of the composition. In some embodiments, the polyvinyl alcohol is present in the compositions in an amount of about 1%, about 2%, about 3%, about 4%, about 5%, about 6%, about 7%, about 8%, about 9%, or about 10% w/w relative to the total weight of the composition. Such solid herbicidal compositions comprises one or more solid, water soluble polymer or oligomer other than polyvinyl alcohol (e.g., sodium lignosulfonate) and the total amount of solid, water soluble polymers or oligomers is greater than about 20% w/w relative to the total weight of the composition.

D. Stability Properties

In some embodiments, the improved solid herbicidal compositions described herein provide improved chemical and physical stability during processing and storage and readily disperse when added to water, in a spray tank prior to spray application or directly to an aquatic environment, such as, for example, a flooded rice paddy or field, where they provide acceptable levels of biological activity when used to control targeted pests. The improved stability of the solid herbicidal compositions described herein includes, but is not limited to, the inhibition of leakage or loss of ingredients contained in the solid herbicidal compositions, particularly liquid ingredients such as liquid active ingredients or liquid built-in adjuvants. The stability of the improved solid herbicidal compositions is particularly improved in instances where a high load (e.g., >150 g/kg or >200 g/kg) of liquid ingredients, such as liquid built-in adjuvants, is present. The improved solid herbicidal compositions described herein provide improved physical stability when stored in a variety of environments, such as, but not limited to, elevated temperature, elevated humidity, and/or high weight compression. In high humidity environments, for example, the improved solid herbicidal compositions have a reduced tendency to cake, stick together or degrade, and/or leak their liquid ingredients, particularly in the presence of high weight compression, such as that encountered during product storage in stacks of flexible containers, such as paper, plastic or cloth bags. The amount of moisture that a particular composition can absorb in an environment of defined temperature and humidity can be described by its equilibrium moisture content.

In some embodiments, the improved solid herbicidal compositions described herein exhibit improved stability at temperatures of greater than or equal to about 54° C. for a period of at least 1, 2, 3, 4, 5, 6, 7, or 8 days, while under weight compression in a low humidity (e.g., <30% relative humidity) environment. In some embodiments, the improved solid herbicidal compositions described herein exhibit improved stability at temperatures of greater than or equal to about 40° C. for a period of at least 1, 2, 3, 4, 5, 6, 7, or 8 days, while under weight compression and in a moderate humidity (e.g., 45% relative humidity) environment. In some embodiments, the improved solid herbicidal compositions described herein exhibit improved stability at ambient temperatures of greater than or equal to about 20° C. for a period of at least 1, 2, 3, 4, 5, 6, 7, or 8 days, while under weight compression and in a high humidity (e.g., 65% relative humidity) environment.

In some embodiments, the improved solid herbicidal compositions described herein provide good stability to high temperature drying conditions (e.g., from about 80° C. to about 150° C.) they are subjected to during preparation, as they readily disperse when poured into water and retain their biological efficacy when applied, for example, by spray application to target weed pests.

In some embodiments, the improved solid herbicidal compositions described herein provide improved stability at temperatures of greater than or equal to about 54° C. for a period of at least 1, 2, 3, 4, 5, 6, 7, 8, 10, 12, or 14 days, and readily disperse when poured into water and retain the same or similar particle size profile as when they are initially prepared.

In other embodiments, the relative stability of the improved solid herbicidal compositions described herein can be determined by thermal analysis. This can be done using a thermoanalytical method, such as Differential Scanning calorimetry (DSC), where the heat flow into or out of a sample relative to an inert standard is measured as the temperature of the sample is slowly increased. Samples that either absorb or produce heat are generally undergoing a chemical or physical transformation, such as, but not limited to, a phase change such as melting, crystallization, or glass transition, a chemical decomposition, an oxidation, or a chemical reaction. The temperatures at which such thermally induced transformations occur are indicative of the relative stability of such compositions. Compositions that have thermal events occurring at lower temperatures are generally less stable than those with thermal events occurring at high temperatures.

E. Methods of preparation

A further aspect of the compositions and methods described herein concerns methods of preparing the improved solid herbicidal compositions. In one embodiment, granule formulations may be produced using one or more of the following processing methods: (1) pan granulation, (2) mixing agglomeration, (3) extrusion granulation, (4) fluid bed granulation, (5) spray granulation or agglomeration, and (6) drum granulation. In some embodiments, granules may be prepared by using a pellet press. The physico-chemical properties of the active ingredient and additives are important to consider when choosing a process to use. G. A. Bell and D. A. Knowles in, "Chemistry and Technology of Agrochemical Formulations," D. A. Knowles, editor, (Kluwer Academic Publishers, 1998), pages 41-114, incorporated herein by reference, describe the types of granules used in agricultural chemical formulations and provide references to the production of these solid formulations. In one embodiment, powder formulations can be produced by vacuum drying, rotary evaporator drying, spray drying, drum drying, or other processing methods that are well known to those of skill in the art.

In any of the processing methods described herein, optional inert ingredients may be added to a composition before, during or after processing to improve the processing or to improve the final quality, stability or dispersion properties in water of the powder or granule. These optional inert ingredients may include, but are not limited to, flowability additives, stability additives such as, for example, antioxidants to stabilize the built-in adjuvant, and anti-caking agents such as, for example, hydrophilic precipitated silicas, hydrophilic fumed silicas and clays, anti-foaming agents, wetting agents, binders, dispersing agents, solid diluents and carriers.

Also provided herein are examples where solid additives are used to stabilize water insoluble liquids during processing to make stable powders. Examples of such additives are gelatin, glycine, casein, water-soluble polymers such as polyvinyl alcohol and polyvinyl pyrrolidone, and polysaccharides. Some of these applications are described, for example, in U.S. Pat. No. 4,244,836 and WO 2006/076943, incorporated herein by reference. There have been, however, very limited efforts to stabilize high levels of built-in adjuvants during processing to produce agricultural granules or powders.

An example of a method of preparing the improved solid herbicidal compositions described herein comprises:

(1) mixing all solid, water soluble polymers or oligomers in water to form an aqueous phase;

(2) mixing the built-in adjuvants and oil soluble or oil dispersible active ingredients to form an oil phase; (3) adding the oil phase prepared in step (2) to the aqueous phase prepared in step (1) under high shear homogenization to provide a mixture; and (4) drying the mixture prepared in (3) to provide the improved solid herbicidal compositions as a granule or a powder.

In some embodiments, the method of preparing the improved solid herbicidal compositions described herein further comprises (5) optionally, agglomerating the herbicidal powder prepared in step (4) by a low shear granulation process to prepare an herbicidal granule.

The most optimal way of practicing the methods described herein to prepare the improved herbicidal granule or powder compositions described herein can easily be determined by one of ordinary skill in the art in view of the present disclosure.

An especially suitable method of preparing the improved solid herbicidal compositions involves taking the mixture obtained in step 3 of the method of preparation described above and spray drying it to provide the improved solid herbicidal compositions in the form of a powder or a granule. The improved powder may be further processed into the improved granule using a low-shear granulation method such as pan granulation, fluid bed agglomeration or spray agglomeration. Use of such low shear processing methods is desired to minimize mechanical damage to the improved granule and loss of the built-in adjuvant.

In another embodiment, provided herein are improved solid herbicidal compositions, such as a granule or a powder, prepared according to a method described herein.

F. Further Embodiments of Active Ingredients

In another embodiment, the improved solid herbicidal compositions described herein further comprise one or more additional agriculturally active ingredients, including pesticide active ingredients, plant growth regulators, or safeners. These pesticide active ingredients, plant growth regulators, and safeners may include one or more of an herbicide, an insecticide, a fungicide, a nematicide, a plant growth regulator, or an herbicide safener.

In one embodiment, suitable herbicides that may be present in the improved solid herbicidal compositions described herein include, but are not limited to, 2,4-D, acetochlor, acifluorfen, alachlor, amidosulfuron, aminopyralid, aminotriazole, ammonium thiocyanate, anilifos, benfuresate, bentazon, benthiocarb, benzobicyclon, benzofenap, bifenox, bromobutide, butachlor, cafenstrole, carfentrazone, chlorimuron, chlorpropham, clomazone, clomeprop, clopyralid, cumyluron, daimuron, diclofop, diflufenican, dimepiperate, dimethametryn, diquat, dithiopyr, EK2612, EPTC, esprocarb, ET-751, ethbenzanid, fenoxaprop-ethyl+isoxidifen-ethyl, fenoxasulfone, fentrazamide, flazasulfuron, flufenacet, flufenpyr, flumioxazin, flupyrsulfuron, fluoroxypyr, fomesafen, foramsulfuron, glufosinate, glyphosate, imazamethabenz, imazapic, imazapyr, imazaquin, indanofan, indaziflam, ioxynil, ipfencarbazone, isoxaben, MCPA, MCPB, mefenacet, mesosulfuron, mesotrione, metolachlor, molinate, monosulfuron, MSMA, orthosulfamuron, oryzalin, oxadiargyl, oxadiazon, oxazichlomefone, oxyfluorfen, paraquat, pendimethalin, pentoxazone, pethoxamid, picloram, pinoxaden, piperophos, pretilachlor, prohexadione, propachlor, propanil, propisochlor, propyzamide, prosulfocarb, prosulfuron, pyributicarb, pyraclonil, pyrazogyl, pyrazolynate, pyrazoxyfen, pyridate, quinoclamine, quinclorac, S-3252, saflufenacil, simazine, simetryne, s-metolachlor, sulcotrione, sulfentrazone, sulfosate, tefuryltrione, tepraloxydim, thenylchlor, thiazopyr, thiobencarb, triclopyr, trifluralin, trinexapac, and tritosulfuron.

In one embodiment, suitable insecticides that may be present in the improved solid herbicidal compositions described herein include, but are not limited to, abamectin, acephate, acetamiprid, acrinathrin, alpha-cypermethrin, alpha-endosulfan, azadirachtin, azinphos-ethyl, azinphos-methyl, bendiocarb, benfuracarb, bensultap, beta-cyfluthrin, beta-cypermethrin, bifenthrin, bufencarb, buprofezin, butacarb, cadusafos, carbaryl, carbofuran, carbosulfan, cartap, cartap hydrochloride, chlorantraniliprole, chlorfenapyr, chlorfenvinphos, chlorfluazuron, chlormephos, chlorpyrifos, chlorpyrifos-methyl, chromafenozide, clothianidin, cyantraniliprole, cyfluthrin, cyhalothrin, cypermethrin, deltamethrin, diazinon, dicrotophos, diflubenzuron, dimethoate dinotefuran, disulfoton, emamectin, emamectin benzoate, endosulfan, endothion, endrin, EPN, esfenvalerate, etaphos, ethiofencarb, ethion, ethiprole, ethoate-methyl, etofenprox, fenamiphos, fenazaflor, fenethacarb, fenitrothion, fenobucarb, fenpropathrin, fensulfothion, fenthion, fenthion-ethyl, fenvalerate, fipronil, flonicamid, flubendiamide, flucythrinate, fonofos, fufenozide, furathiocarb, gamma-cyhalothrin, gamma-HCH, halfenprox, halofenozide, heptenophos, hyquincarb, imidacloprid, indoxacarb, isazofos, isobenzan, isocarbophos, isofenphos, isofenphos-methyl, isoprocarb, isothioate, isoxathion, kinoprene, lambda-cyhalothrin, lepimectin, lufenuron, malathion, methamidophos, methomyl, methoxyfenozide, mevinphos, mexacarbate, milbemectin, monocrotophos, nitenpyram, novaluron, omethoate, oxamyl, oxydemeton-methyl, oxydeprofos, oxydisulfoton, parathion, parathion-methyl, penfluoron, permethrin, phenthoate, phorate, phosalone, phosfolan, phosmet, phosphamidon, pirimetaphos, pirimicarb, pirimiphos-ethyl, pirimiphos-methyl, primidophos, profenofos, profluthrin, promecarb, propaphos, propoxur, prothiofos, pymetrozine, pyrafluprole, pyridalyl, pyrifluquinazon, pyriprole, pyriproxyfen, spinetoram, spinosad, spirotetramat, sulfoxaflor, sulprofos, tau-fluvalinate, tebufenozide, tebufenpyrad, teflubenzuron, tefluthrin, tetramethylfluthrin, theta-cypermethrin, thiacloprid, thiamethoxam, thicrofos, thiocyclam, thiocyclam oxalate, thiodicarb, thiometon, thiosultap, thiosultap-disodium, thiosultap-monosodium, thuringiensin, tolfenpyrad, triazophos, triflumuron, and zeta-cypermethrin.

In one embodiment, suitable fungicides that may be present in the improved solid herbicidal compositions described herein include, but are not limited to, tricyclazole, phthalide, carpropamide, pyroquilon, diclocymet, fenoxanil, probenazole, isoprothiolane, iprobenfos, isotianil, tiadinil, kasugamycin, flutolanil, mepronil, pencycuron, polyoxins, validamycin, toclophos-methyl, boscalid, penthiopyrad, thifluzamide, bixafen, fluopyram, isopyrazam, propiconazole, difenoconazole, fenbuconazole, ipconazole, triadimefon, hexaconazole, azoxystrobin, metaminostrobin, orysastrobin, and acibenzolar-S-methyl. In one embodiment, some of these fungicides may not be effective for disease control when applied at the timing of an herbicide granule application because fungal disease propagation and growth cycles may not match the targeted weed growth cycles. The effective use and application timing of these fungicides can be easily determined by one of skill in the art.

In one embodiment, suitable herbicide safeners that may be present in the improved solid herbicidal compositions include, but are not limited to, benoxacor, benthiocarb, cloquintocet, cloquintocet-mexyl, daimuron, dichlormid, dicyclonon, dimepiperate, fenchlorazole-ethyl, fenclorim, flurazole, fluxofenim, furilazole, harpin proteins, isoxadifen-ethyl, mefenpyr-diethyl, mephenate, MG 191, MON 4660, naphthalic anhydride (NA), oxabetrinil, 829148, and N-phenyl-sulfonylbenzoic acid amides.

In some embodiments, the improved solid herbicidal compositions described herein contain, relative to the total composition, from about 0.1 g/kg to about 100 g/kg, from about 1 g/kg to about 100 g/kg, or from about 1 g/kg to about 50 g/kg of cloquintocet or cloquintocet-mexyl.

In some embodiments, the improved solid herbicidal compositions described herein contain, on a weight basis relative to the herbicide active ingredient(s), from about 0.5 to about 3 times, from about 0.5 to about 2 times, or from about 0.5 to about 1 times the amount of cloquintocet or cloquintocet-mexyl. In some embodiments, the improved solid herbicidal compositions described herein contain cloquintocet or cloquintocet-mexyl in an amount on a weight basis, from about 0.5 to about 3 times, from about 0.5 to about 2 times, or from about 0.5 to about 1 times, relative to other herbicide active ingredient(s).

In some embodiments, suitable plant growth regulators that may be present in the improved solid herbicidal compositions described herein include, but are not limited to, 2,4-D, 2,4-DB, IAA, IBA, naphthaleneacetamide, α-naphthaleneacetic acid, kinetin, zeatin, ethephon, aviglycine, 1-methylcyclopropene (1-MCP), ethephon, gibberellins, gibberellic acid, abscisic acid, ancymidol, flurprimidol, mefluidide, paclobutrazol, tetcyclacis, uniconazole, brassinolide, brassinolide-ethyl, and ethylene.

In some embodiments, the improved solid herbicidal compositions described herein contain the herbicide compound of the Formula

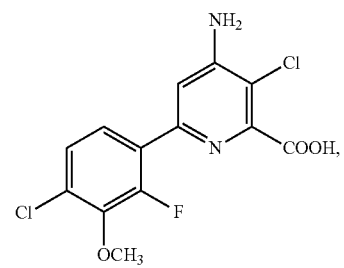 [SMILES: COc1c(Cl)ccc(-c2cc(N)c(Cl)c(C(=O)O)n2)c1F]

or a $C_1$-$C_6$ alkyl ester or salt derivative thereof, such as, for example, the methyl ester which is referred to herein as Compound A, and at least one of chloransulam-methyl, diclosulam, florasulam, flumetsulam, metosulam, penoxsulam, pyroxsulam, 2,4-D, aminopyralid, clopyralid, diflufenican, fluoroxypyr-meptyl, picloram, or propyzamide, or derivatives thereof, and, optionally, the herbicide safener cloquintocet or cloquintocet-mexyl.

In some embodiments, the improved solid herbicidal compositions described herein contain the herbicide Compound A, and florasulam, and, optionally, the herbicide safener cloquintocet-mexyl.

In some embodiments, the improved solid herbicidal compositions described herein contain the herbicide compound of the Formula

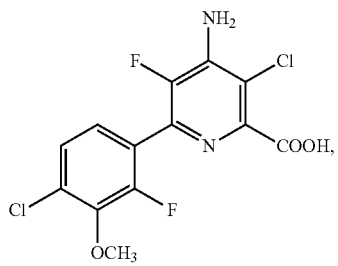

or a $C_1$-$C_{12}$ alkyl or $C_7$-$C_{12}$ arylalkyl ester or salt derivative thereof, such as, for example, the benzyl ester, and at least one of 2,4-D, benfuresate, benzobicyclon, bromobutide, butachlor, clomazone, daimuron, ipfencarbazone, MCPA, MCPB, mefenacet, molinate, orthosulfamuron, oxadiargyl, oxadiazon, oxazichlomefone, pentoxazone, pethoxamid, pretilachlor, propanil, pyributicarb, pyraclonil, pyrazolynate, quinclorac, tefuryltrione, thenylchlor, thiobencarb, or triclopyr, or derivatives thereof.

In some embodiments, the improved solid herbicidal compositions described herein contain the herbicide cyhalofop-butyl, and penoxsulam.

G. Additional Compatible Ingredients

In addition to the compositions and methods set forth above, the improved solid herbicidal compositions described herein may be used in combination with one or more additional compatible ingredients. These additional compatible ingredients may include, for example, one or more agrochemical active ingredients, surfactants, dyes, fertilizers, micronutrients, pheromones, and many other additional ingredients providing functional utility, such as, for example, stabilizers such as antioxidants to stabilize the built-in adjuvant, fragrants and dispersants. When the improved solid herbicidal compositions described herein are used in combination with additional active ingredients, the presently claimed compositions can be formulated with the other active ingredient or active ingredients as solid compositions, tank mixed in water with the other active ingredient or active ingredients for spray application or applied sequentially with the other active ingredient or active ingredients in separate solid or spray applications.

Surfactants conventionally used in the art of formulation and which may optionally be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81, both incorporated herein by reference. These surface-active agents can be anionic, cationic or nonionic in character and can be employed as emulsifying agents, wetting agents, suspending agents, or for other purposes. Typical surface-active agents include, but are not limited to, salts of alkyl sulfates, such as diethanol-ammonium lauryl sulfate; alkylarylsulfonate salts, such as calcium dodecylbenzene-sulfonate; alkylphenol-alkylene oxide addition products, such as nonylphenol-$C_{18}$ ethoxylate; soaps, such as sodium stearate; alkyl-naphthalene-sulfonate salts, such as sodium dibutyl-naphthalenesulfonate; dialkyl esters of sulfo-succinate salts, such as sodium di(2-ethylhexyl) sulfo-succinate; quaternary amines, such as lauryl trimethyl-ammonium chloride; block copolymers of ethylene oxide and propylene oxide; and salts of mono and dialkyl phosphate esters.

Oftentimes, some of these surfactants can be used interchangeably as an agricultural adjuvant, as a liquid carrier or as a surface active agent.

In one embodiment, the improved solid herbicidal compositions provided herein contain no mineral type powder (e.g., clay). In one embodiment, the improved solid herbicidal compositions provided herein contain mineral type powder (e.g., clay) in an amount of less than about 60%, less than about 50%, less than about 40%, less than about 30%, less than about 25%, less than about 20%, less than about 15%, less than about 10%, or less than about 5% w/w relative to the total weight of the composition.

H. Methods for Controlling Weeds

Another embodiment of the compositions and methods described herein concerns a method of controlling weeds by broadcasting or adding the improved solid herbicidal compositions or spraying an aqueous solution or mixture made from the improved solid herbicidal compositions into aquatic environments, such as rice paddies, ponds, lakes and streams, and the like, for the control of undesirable vegetation. In one embodiment, an herbicidally effective amount of the improved solid herbicidal composition, or an aqueous spray solution or mixture made from the improved solid herbicidal compositions is applied to an area of water to provide suitable control of undesirable weed plants. The improved solid herbicidal compositions or spray solutions or mixtures made from the improved solid herbicidal compositions are particularly useful for the control of grass, broadleaf and sedge weeds in flooded rice paddies or fields.

Another embodiment of the compositions and methods described herein concerns a method of controlling undesirable vegetation which comprises adding the described improved solid herbicidal compositions to a carrier such as water and using the resulting water solution or mixture containing the dispersed herbicidal active ingredient for spray application to control undesirable vegetation in crop or non-crop environments. In one embodiment, an herbicidally effective amount of the aqueous spray mixture derived from the improved solid herbicidal compositions is applied, for example, to an area of soil or targeted plant foliage to provide suitable control of undesirable plant pests. Spray solutions or mixtures made from the improved solid herbicidal compositions are particularly useful for the control of grass and/or broadleaf weeds in cereal crop fields.

In one embodiment, provided herein is a method of controlling undesirable vegetation in an aquatic environment, which comprises broadcasting, spraying or adding an herbicidally effective amount of a solid herbicidal composition provided herein, to the aquatic environment either before emergence or after emergence of the undesirable vegetation.

In one embodiment, provided herein is a method of controlling undesirable vegetation in a flooded rice paddy, which comprises broadcasting, spraying or adding an herbicidally effective amount of a solid herbicidal composition provided herein, to the flooded rice paddy either before emergence or after emergence of the undesirable vegetation.

In another embodiment, the improved solid herbicidal compositions described herein can additionally be employed to control undesirable vegetation in many crops that have been made tolerant to or resistant to them or to other herbicides by genetic manipulation or by mutation and selection. The described compositions can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. In some embodiments, it is generally preferred to use the described compositions in combination with herbicides that are selective for the crop being treated and which complement the spectrum of weeds controlled by these compounds at the application rate employed. In some embodiments, it is further generally preferred to apply the described compositions and other complementary herbicides at the same time, either as a combination formulation or as a tank-mix. Similarly, the described compositions can be used in conjunction with acetolactate synthase inhibitors on acetolactate synthase inhibitor tolerant crops.

I. Additional Embodiments

In an exemplary procedure for preparing the improved solid herbicidal compositions, an aqueous phase is prepared by mixing in water the water soluble or water dispersible ingredients including, but not limited to, the solid, water soluble polymers or oligomers and, optionally, any active ingredients or additional inert ingredients. An oil phase is prepared by mixing together any oil soluble ingredients including, but not limited to, built-in adjuvants and oil soluble active ingredients or additional inert ingredients. The oil phase is slowly added into the aqueous phase under high shear homogenization until the desired mixture is achieved. The mixture is then dried to provide the improved solid herbicidal composition in the form of a granule or a powder. The powder can, optionally, be further processed to provide a granular form of the improved solid herbicidal compositions described herein. In one embodiment, provided herein are solid herbicidal compositions prepared according to a procedure described herein.

In an exemplary embodiment, a solid herbicidal composition containing built-in adjuvant provided herein comprises:
a) herbicide active ingredient comprising cyhalofop-butyl, in an amount of from about 2 g/kg to about 75 g/kg (e.g., from about 10 g/kg to about 60 g/kg) relative to the total composition;
b) herbicide active ingredient comprising penoxsulam, in an amount of from about 0 g/kg to about 20 g/kg (e.g., from about 0 g/kg to about 5 g/kg) relative to the total composition;
c) built-in adjuvant comprising methyl soyate, in an amount of from about 300 g/kg to about 600 g/kg (e.g., from about 350 g/kg to about 450 g/kg) relative to the total composition;
d) solid, water soluble polymer or oligomer comprising an 87-99% hydrolyzed polyvinyl alcohol, in an amount of from about 10 g/kg to about 100 g/kg (e.g., about 20 g/kg) relative to the total composition;
e) solid, water soluble polymer or oligomer comprising sodium lignosulfonate, in an amount of from about 150 g/kg to about 600 g/kg (e.g., from about 450 g/kg to about 550 g/kg) relative to the total composition; and
f) optionally, other inert formulation ingredients;
and wherein the solid herbicidal composition does not comprise solid carbohydrate.

In an exemplary embodiment, a solid herbicidal composition containing built-in adjuvant provided herein comprises:
a) herbicide active ingredient comprising Compound A, in an amount of from about 2 g/kg to about 75 g/kg (e.g., from about 5 g/kg to about 30 g/kg) relative to the total composition;
b) herbicide active ingredient comprising florasulam, in an amount of from about 0 g/kg to about 50 g/kg (e.g., from about 2 g/kg to about 25 g/kg) relative to the total composition;
c) built-in adjuvant comprising Agnique ME 12-18, in an amount of from about 300 g/kg to about 700 g/kg (e.g., from about 500 g/kg to about 700 g/kg) relative to the total composition;
d) solid, water soluble polymer or oligomer comprising an 87-99% hydrolyzed polyvinyl alcohol, in an amount of from about 10 g/kg to about 100 g/kg (e.g., about 20 g/kg) relative to the total composition;
e) solid, water soluble polymer or oligomer comprising sodium lignosulfonate, in an amount of from about 150 g/kg to about 600 g/kg (e.g., from about 250 g/kg to about 500 g/kg) relative to the total composition;
f) optionally, cloquintocet (e.g., in an amount of from about 5 g/kg to about 30 g/kg relative to the total composition); and
g) optionally, other inert formulation ingredients;
and wherein the solid herbicidal composition does not comprise solid carbohydrate.

In addition, the improved solid herbicidal compositions described herein may optionally be blended with other granule or powder compositions containing additional active ingredients to form compositions containing, for example, a physically uniform blend of granules or a physically uniform blend of powders. These blends of granule and powder compositions containing two or more active ingredients may be used, for example, to control undesirable weeds in aquatic environments such as flooded rice paddies and fields.

J. Examples

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the present disclosure.

Example 1

Preparation of Improved Solid Herbicidal Compositions That Are Powders Containing Cyhalofop-butyl and High Levels of a Built-in Adjuvant An oil phase was prepared by dissolving 5.4 grams of cyhalofop-butyl in 39.4 grams of methyl soyate (built-in adjuvant; Agnique® ME 18S-U; Cognis). An aqueous phase was prepared by dissolving 10 grams of a 20% (w/w) aqueous solution of Selvol® 205 (polyvinyl alcohol; Sekisui Chemical Co., Ltd.) and 51.5 grams of sodium lignosulfonate (Borresperse® NA; Borregaard LignoTech) in 95.64 grams of water. The oil phase was then slowly added to the aqueous phase while mixing with a Silverson high shear mixer for 30 minutes at approximately 11,000 rpm to produce a mixture of dispersed oil droplets in water with a volume mean diameter ($d_{50}$) of about 1-2 microns as measured using a Malvern Mastersizer 2000 laser diffraction particle analyzer. Once the desired droplet size was obtained, the mixture was spray dried in a BUCHI 290 spray dryer with a feed rate of 300 mL/hr (inlet temp.: 135° C.; outlet temp.: 90° C.) to provide a dried solid (Powder A; Table 1) with a residual water content of 2 to 3 weight percent with respect to the total sample weight. The volume mean diameter of the solid particles produced from Powder A ranged from 2 to 4 microns upon re-dispersion of Powder A in water. Silica (1.5 g; Hi-Sil™ 233, available from PPG Industries Inc., Monroeville, Pa.) was added to Powder A to improve its flow characteristics. Powder B and Comparative Powder C were prepared in a similar manner to Powder A using the ingredients shown in Table 1. Also in a similar manner to Powder A and using the ingredients shown in Table 1, Powder A1 and Powder A2 (both containing penoxsulam) were prepared by adding Granite SC Herbicide (240 g/L penoxsulam; Dow AgroSciences) to the pre-spray dried, aqueous-oil mixture above containing cyhalofop-butyl.

TABLE 1

Composition of Powders A, A1, A2, B, and Comparative Powder C

| Ingredients | Powder A (Wt %) | Powder A1 (Wt %) | Powder A2 (Wt %) | Powder B (wt %) | Comparative Powder C (wt %) |
|---|---|---|---|---|---|
| cyhalofop-butyl (CB) | 5.4 | 3.6 | 1.8 | 1.35 | 1.35 |
| impurity in tech. CB | 0.2 | 0.13 | 0.07 | 0.05 | 0.05 |
| penoxsulam | 0 | 0.48 | 0.24 | 0 | 0 |
| methyl soyate (built-in adjuvant) | 39.4 | 41.27 | 43.13 | 43.6 | 43.6 |
| sodium lignosulfonate | 51.5 | 50.46 | 50.83 | 53 | 21 |
| sucrose (carbohydrate) | 0 | 0 | 0 | 0 | 32 |
| polyvinyl alcohol | 2 | 2 | 2 | 2 | 2 |
| citric acid | 0 | 1.78 | 1.79 | 0 | 0 |
| inerts in Granite SC herbicide | 0 | 0.28 | 0.14 | 0 | 0 |
| silica | 1.5 | 0 | 0 | 0 | 0 |

Example 2

Preparation of Improved Solid Herbicidal Compositions That Are Powders Containing Compound A, Florasulam, Cloquintocet-mexyl and a High Level of Built-in Adjuvant Using the ingredients and amounts shown in Table 2, Powders D-G were prepared as described. An oil phase was prepared by dissolving (with heating and sonication if necessary) or dispersing (with very high shear mixing) Compound A and cloquintocet-mexyl (CQM) in Agnique ME 12-18 (built-in adjuvant). An aqueous phase was prepared by dissolving sodium lignosulfonate (Borresperse NA; Lignotech, Inc.) and polyvinyl alcohol (PVA; Selvol™ 205; Sekisui Specialty Chemicals America, LLC) in water. The oil phase was slowly added into the aqueous phase while mixing with a Silverson high shear mixer at approximately 3000 rpm if the oil loading is below 60 dry wt %, or at 6000 rpm if the oil loading is above 60 dry wt %, until the volume mean particle size ($d_{50}$) of the emulsion droplets was about 5-10 microns (m). Once the desired emulsion size was obtained, a suspension of florasulam in water (45 wt %) was added with mixing to provide a suspoemulsion. The suspoemulsion was stirred with a magnetic stir bar and was dried by feeding it into a Buchi 290 spray dryer with an inlet temperature of 135° C. at a liquid flow rate of 300 mL/hr. The spray dried powder obtained had a moisture content of 3-5 wt % and upon redispersion in water showed a similar particle size profile to the emulsion from which it was produced.

TABLE 2

Composition of Powders D, E, F and G

| Ingredients | Powder D (Wt %) | Powder E (Wt %) | Powder F (Wt %) | Powder G (Wt %) |
|---|---|---|---|---|
| Compound A | 0.64 | 1.28 | 2.55 | 0.64 |
| Florasulam | 0.50 | 1.00 | 2.00 | 0.5 |
| CQM | 0.62 | 1.24 | 2.47 | 0.62 |
| Agnique ME 12-18 (built-in adjuvant) | 50.00 | 50.00 | 50.00 | 70 |
| polyvinyl alcohol | 2.00 | 2.00 | 2.00 | 2 |
| sodium lignosulfonate | 46.24 | 44.49 | 40.97 | 26.24 |
| Total | 100.00 | 100.00 | 100.00 | 100.00 |

Example 3

Stability Testing of Improved Solid Herbicidal Compositions

Compression-Humidity Testing:

Powder B and Comparative Powder C were subjected to compression testing in environments of varying temperature and humidity.

Testing procedure: 10 g samples of Powder B and Comparative Powder C were placed in separate cylindrical glass containers (150 mL glass beakers with 4.5 cm inside diameter). About 835 g of weight was placed on the powder samples (52.53 g/cm$^2$) by placing a glass bottle (slightly less than 4.5 cm diameter) filled with metal beads onto the powders. Each of these samples was then placed in 3 different storage conditions for 8 days each: (1) 54 @<30% relative humidity, (2) room temperature @ 65% relative humidity, and (3) 40° C. @ 45% relative humidity. All three samples were inspected for caking stability and leakage of the oil adjuvant (methyl soyate) after 8 days of storage and the results are listed in the Table 3. In a manner similar to that described here, other improved solid herbicidal compositions described herein can be tested for storage stability in high compression and humid conditions.

TABLE 3

Storage Stability of Powder B and Comparative Powder C in High Compression (52.53 g/cm$^2$) and Humid Conditions

| Storage Conditions | Powder B (0 wt % sucrose) Storage Stability Scoring[1] | Comparative Powder C (32 wt % sucrose) Storage Stability Scoring[1] |
|---|---|---|
| 54° C./8 days/ <30% relative humidity | 1 | 4 |
| room temperature/8 days/ 65% relative humidity | 1 | 5 |
| 40° C./8 days/ 45% relative humidity | 2 | 5 |

[1]Storage stability scoring:
1-High Stability (no or slight caking to form lumps that are easily converted back to the powder with slight pressure; no leakage of oil adjuvant);
2-Moderate Stability (moderate caking to form lumps that are converted back to the powder with moderate pressure; no leakage of oil adjuvant);
3-Low Stability (extensive caking to form hard lumps that are converted back to the powder with high pressure; no leakage of oil adjuvant);
4-Unstable (severe caking to form lumps that do not fall apart with high pressure; some leakage of oil adjuvant);
5-Very Unstable (severe caking to form a hard glass; extensive leakage of contained oil adjuvant).

Redispersion of the Improved Solid Herbicidal Compositions in Water:

The particle size distribution of Powder E and several samples of Powder E that had been stored at 54° C. were determined by dispersing the samples in water and measuring the particle size distribution using a Malvern Mastersizer 2000 (data shown in Table 4). The data indicates that Powder E was very stable to both the preparation and storage conditions.

TABLE 4

Particle Size Analysis of Powder E after Accelerated Storage at 54° C. and Re-dispersion in Water

| Storage Conditions | Particle Size (μm) d(0.5) |
|---|---|
| Initial | 2.4 |
| 5 days @ 54° C. | 2.5 |
| 10 days @ 54° C. | 2.5 |
| 15 days @ 54° C. | 2.3 |

Differential Scanning Calorimetry Analyses:

Powder B and Comparative Powder C were analyzed by Differential scanning calorimetry (DSC) on a TA Instruments DSC Analyzer (Model Q2000). As shown in FIG. 1, the two samples exhibited distinctly different thermal property profiles as indicated by the occurrence of the various thermal events (endotherms and exotherms) at different temperatures. Because the thermal events exhibited by Powder B occurred at a much higher temperature than those exhibited by Powder C, Powder B is indicated by this method to have better stability. These results are in agreement with the storage stability test results shown in Table 3.

Example 4

Use of the Improved Solid Herbicidal Compositions that are Powders Containing High Levels of Built-in Adjuvant for Weed Control Materials and Methods:
Plant Propagation A peat based potting soil, Metro-mix 360®, was used as the soil media in this experiment. Metro-mix is a growing medium consisting of 35 to 45% specially processed Coconut Coir Pith, 10 to 20% horticultural grade vermiculite, 15 to 25% processed Ash Bark, 20 to 30% choice Canadian Sphagnum Peat Moss and proprietary nutrients and other ingredients. Several seeds of each species were planted each in separate 10 cm square pots. Plant material was propagated in greenhouse zone E2, Dow AgroSciences Global Headquarters (Indianapolis, Ind., USA) and held at a temperature of 18 to 20° C. and relative humidity of 50 to 60%. Natural light was supplemented with 1000-watt metal halide overhead lamps with an average illumination of 500 μm-2 s-1 photosynthetic active radiation for 16 hours each day. Plants were top-watered prior to treatment and sub-irrigated after treatment.

Herbicide Application

Treatments were applied with a track sprayer, manufactured by Allen Machine Works (Midland, Mich.). The track sprayer was calibrated to deliver 94 L/ha utilizing an 8002E even fan spray nozzle at 40 psi pressure at a speed of 1.9 mph (3.1 km/hr). Appropriate amounts of formulated product were added to spray vials as calculated by the software package ARM8 (Gylling Data Management Inc.). Herbicide aliquots were diluted with clean Indianapolis tap water to a total volume of 60 mL. No adjuvants were added to the spray solution. The treatments were evaluated 20 days after spray application and the data is expressed in percent control of the four weed species (Table 5).

Weed Species Evaluated:

| Weed | Latin name | Bayer Code | Growth Stage |
|---|---|---|---|
| Redroot Pigweed | Amaranthus retroflexus | AMARE | 3 to 4 leaf |
| Common lambsquarters | Chenopodium album | CHEAL | 6 to 8 leaf |
| Flixweed | Descurainia sophia | DESSO | 4 to 6 leaf |
| Common Chickweed | Stellaria media | STEME | 4 to 6 leaf |

TABLE 5

Percent Control of Weeds 20 Days after Spray Application of the Compositions Described Herein

| Composition | Rate (g ae/ha)[1] | Percent Weed Control | | | |
|---|---|---|---|---|---|
| | | CHEAL | AMARE | STEME | DESSO |
| OD Standard[2] | 2.75 + 2.3 + 2.75 | 58 | 98 | 99 | 100 |
| OD Standard | 5.5 + 4.6 + 5.5 | 82 | 99 | 100 | 100 |
| OD Standard | 11 + 9.2 + 11 | 92 | 99 | 100 | 100 |
| Powder D | 2.75 + 2.3 + 2.75 | 70 | 72 | 99 | 100 |
| Powder D | 5.5 + 4.6 + 5.5 | 84 | 90 | 100 | 100 |
| Powder D | 11 + 9.2 + 11 | 94 | 96 | 100 | 100 |
| Powder E | 2.75 + 2.3 + 2.75 | 68 | 81 | 99 | 99 |
| Powder E | 5.5 + 4.6 + 5.5 | 86 | 96 | 99 | 100 |
| Powder E | 11 + 9.2 + 11 | 91 | 92 | 100 | 100 |
| Powder F | 2.75 + 2.3 + 2.75 | 49 | 74 | 100 | 98 |
| Powder F | 5.5 + 4.6 + 5.5 | 75 | 94 | 100 | 100 |
| Powder F | 11 + 9.2 + 11 | 88 | 98 | 100 | 100 |

[1]Rates shown are for Compound A + florasulam + cloquintocet-mexyl in grams acid equivalent per hectare (g ae/ha);
[2]OD Standard: Compound A + florasulam + cloquintocet-mexyl (6 + 5 + 6 g ae/L in methylated seed oil solvent).

What is claimed:
1. A solid herbicidal composition comprising:
   a) at least one herbicide selected from the class of ACCase and ALS enzyme inhibitors and compounds of the Formula

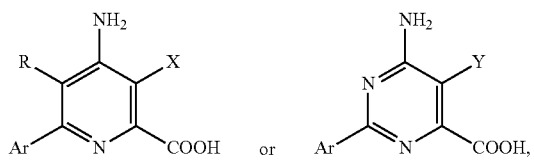

wherein
- Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;
- R represents H or F;
- X represents Cl or vinyl; and Y represents Cl, vinyl or methoxy;

and their salts and esters;
wherein the herbicide(s) is present in the composition in an amount of from about 1 gram per kilogram (g/kg) to about 200 g/kg relative to the total weight of the composition;
  b) one or more built-in adjuvant, wherein the built-in adjuvant(s) is present in the composition in an amount of from about 50 g/kg to about 750 g/kg relative to the total weight of the composition, wherein the built-in adjuvant is a non-ionic surfactant or water-immiscible liquid; and
  c) one or more solid, water soluble polymer or oligomer, wherein the solid, water soluble polymer(s) or oligomer(s) is present in the composition in an amount of from about 200 g/kg to about 700 g/kg relative to the total weight of the composition;
wherein the composition does not comprise solid carbohydrate,
wherein when the one or more solid, water soluble polymers or oligomers comprises polyvinyl alcohol, the polyvinyl alcohol is present in the composition in an amount less than 7% by weight relative to the total weight of composition;
wherein the composition exhibits less caking and adjuvant leaking when stored at 40° C. at 45% relative humidity over eight days, than an otherwise same composition further comprising sucrose in an amount from 10 g/kg to 700 g/kg relative to the total weight of the composition; or
wherein the composition is exhibits greater stability at higher temperatures, as measured by DSC, than an otherwise same composition further comprising sucrose in an amount from 10 g/kg to 700 g/kg relative to the total weight of the composition.

2. The composition of claim 1, wherein the solid herbicidal composition is a powder.

3. The composition of claim 1, wherein the solid herbicidal composition is a granule.

4. The composition of claim 1, further comprising one or more additional inert ingredients.

5. The composition of claim 1, further comprising one or more additional agriculturally active ingredients.

6. The composition of claim 1, in which the herbicide is at least one of cyhalofop-butyl; penoxsulam; bensulfuron-methyl; azimsulfuron; imazosulfuron; fenoxaprop-P-ethyl; the compound of Formula

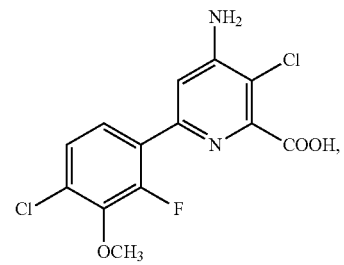

or a $C_1$-$C_6$ alkyl ester or salt thereof; or the compound of Formula

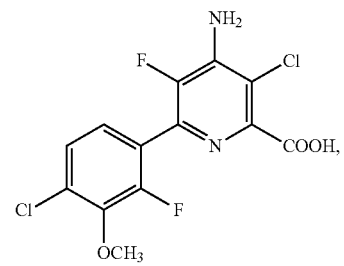 [SMILES: COc1c(Cl)ccc(-c2nc(C(=O)O)c(Cl)c(N)c2F)c1F]

or a $C_1$-$C_{12}$ alkyl or $C_7$-$C_{12}$ arylalkyl ester or salt thereof.

7. The composition of claim 1, in which the herbicide is at least one of cyhalofop-butyl; penoxsulam; bensulfuron-methyl; the compound of Formula

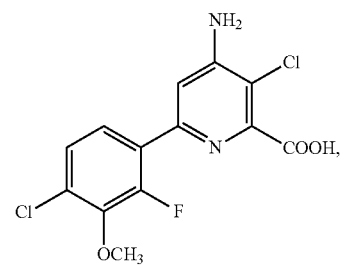 [SMILES: COc1c(Cl)ccc(-c2cc(N)c(Cl)c(C(=O)O)n2)c1F]

or a $C_1$-$C_6$ alkyl ester or salt thereof; or the compound of Formula

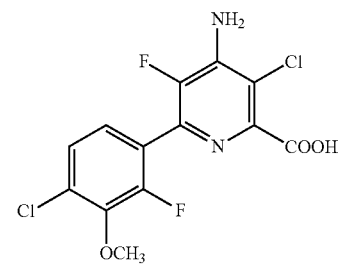 [SMILES: COc1c(Cl)ccc(-c2nc(C(=O)O)c(Cl)c(N)c2F)c1F]

or a $C_1$-$C_{12}$ alkyl or $C_7$-$C_{12}$ arylalkyl ester or salt thereof.

8. The composition of claim 1, in which the built-in adjuvant comprises one or more of water-immiscible organic liquid.

9. The composition of claim 1, in which the built-in adjuvant comprises one or more of a petroleum derived paraffinic hydrocarbon, a petroleum derived aromatic hydrocarbon, a plant derived oil, or a $C_1$-$C_6$ ester of a plant derived oil.

10. The composition of claim 1, in which the build-in adjuvant comprises one or more of a seed oil, or a $C_1$-$C_6$ ester of plant derived oil.

11. The composition of claim 1, in which the build-in adjuvant comprises methyl soyate.

12. The composition of claim 1, wherein the build-in adjuvant is in an amount of from about 200 g/kg to about 600 g/kg relative to the total weight of the composition.

13. The composition of claim 1, wherein the build-in adjuvant is in an amount of from about 300 g/kg to about 600 g/kg relative to the total weight of the composition.

14. The composition of claim 1, in which the solid, water soluble polymer or oligomer is selected from the group consisting of one or more lignosulfonates, polyvinyl alcohols with a degree of hydrolysis from about 87 to about 99 percent, alkyl naphthalene sulfonate formaldehyde condensates, and mixtures thereof.

15. The composition of claim 1, in which the solid, water soluble polymer or oligomer comprises one or more of polyvinyl alcohols or lignosulfonates.

16. The composition of claim 1, in which the solid, water soluble polymer or oligomer comprises one or more of polyvinyl alcohols derived from the hydrolysis of polyvinyl acetate, that vary in the degree of hydrolysis from about 87 to about 99%.

17. The composition of claim 1, wherein the solid, water soluble polymer or oligomer is in an amount of from about 300 g/kg to about 600 g/kg relative to the total weight of the composition.

18. The composition of claim 1, which comprises no polyvinyl alcohol, or which comprises polyvinyl alcohol wherein the polyvinyl alcohol has a degree of hydrolysis from about 87 to about 99 percent.

19. The composition of claim 1, which comprises mineral powder in an amount of less than about 60% w/w relative to the total weight of the composition.

20. A method of controlling undesirable vegetation in an aquatic environment, which comprises broadcasting, spraying or adding an herbicidally effective amount of the composition of claim 1, to the aquatic environment either before emergence or after emergence of the undesirable vegetation.

21. A method of controlling undesirable vegetation in a flooded rice paddy, which comprises broadcasting, spraying or adding an herbicidally effective amount of the composition of claim 1, to the flooded rice paddy either before emergence or after emergence of the undesirable vegetation.

22. A method of preparing the solid herbicidal composition of claim 1, in the form of a granule or a powder which comprises:
   a) mixing the solid, water soluble polymers or oligomers in water to form an aqueous phase;
   b) mixing the built-in adjuvant and the at least one herbicide according to claim 1 to form an oil phase;
   c) adding the oil phase prepared in step b) to the aqueous phase prepared in step a) under high shear homogenization to provide a mixture;
   d) drying the mixture prepared in c) to provide an herbicidal powder or an herbicidal granule; and
   e) optionally, agglomerating the herbicidal powder prepared in d) by a low shear granulation process to prepare an herbicidal granule, wherein
   the built-in adjuvant is a non-ionic surfactant or water-immiscible liquid; and
   when the one or more solid, water soluble polymers or oligomers comprises polyvinyl alcohol, the polyvinyl alcohol is present in the composition in an amount less than 7% by weight relative to the total weight of composition.

23. The composition according to claim 1, wherein the polyvinyl alcohol, if present, is present in an amount of less than 5% by weight relative to the total weight of the composition.

24. The composition according to claim 1, wherein the polyvinyl alcohol, if present, is present in an amount of less than 3% by weight relative to the total weight of the composition.

25. The composition according to claim 1, wherein the polyvinyl alcohol, if present, is present in an amount of less than 1% by weight relative to the total weight of the composition.

26. The composition of claim 1, which comprises no mineral powder.

27. The composition of claim 1, comprising a water immiscible liquid built-in adjuvant in an amount greater than 150 g/kg relative to the total weight of the composition.

* * * * *